United States Patent [19]

Wojdani

[11] Patent Number: 5,049,390

[45] Date of Patent: * Sep. 17, 1991

[54] LIPOSOME CONTAINING IMMUNOTHERAPY AGENTS FOR TREATING IGE MEDIATED ALLERGIES

[75] Inventor: Aristo Wojdani, Los Angeles, Calif.

[73] Assignee: Allergy Immuno Technologies, Inc., Newport Beach, Calif.

[*] Notice: The portion of the term of this patent subsequent to Aug. 7, 2007, has been disclaimed.

[21] Appl. No.: 515,650

[22] Filed: Apr. 25, 1990

Related U.S. Application Data

[63] Continuation of Ser. No. 92,032, Sep. 2, 1987, abandoned.

[51] Int. Cl.$^5$ ............................................. A61K 37/22
[52] U.S. Cl. .................................................... 424/450
[58] Field of Search ......................................... 424/450

[56] References Cited

U.S. PATENT DOCUMENTS 4,235,871 11/1980 Papahadjopoulous et al. .... 424/450
4,241,046 12/1980 Papahadjopoulous et al. .... 424/420
4,663,167 5/1987 Lopez-Berestein et al. ......... 514/37

OTHER PUBLICATIONS

Chemical Abstracts 94:154477p; 95:4950µ.
Connor, et al., "Monoclonal Antibody and Liposomes", *Pharmac. Ther.*, vol. 22, pp. 341-365 (1985).
Chemical Abstracts 105(4): 30052X; 104(6): 39758µ, 101(16): 137035p; 93(11): 109745t; 99(24): 200444d; 89(17): 142264a.
Ostro, M., "Liposomes", *Scientific American*, Jan. 1987, pp. 103-111.

*Primary Examiner*—Olik Chaudhuri
*Assistant Examiner*—Andrew Griffis
*Attorney, Agent, or Firm*—James A. Quinton; Frank Frisenda, Jr.

[57] ABSTRACT

An immunotherapy agent for the treatment of allergy composed of an allergen encapsulated in or covalently bound to a liposome is disclosed. Use of the agent in immunotherapy results in enhanced IgG production and reduced IgE production.

11 Claims, 1 Drawing Sheet

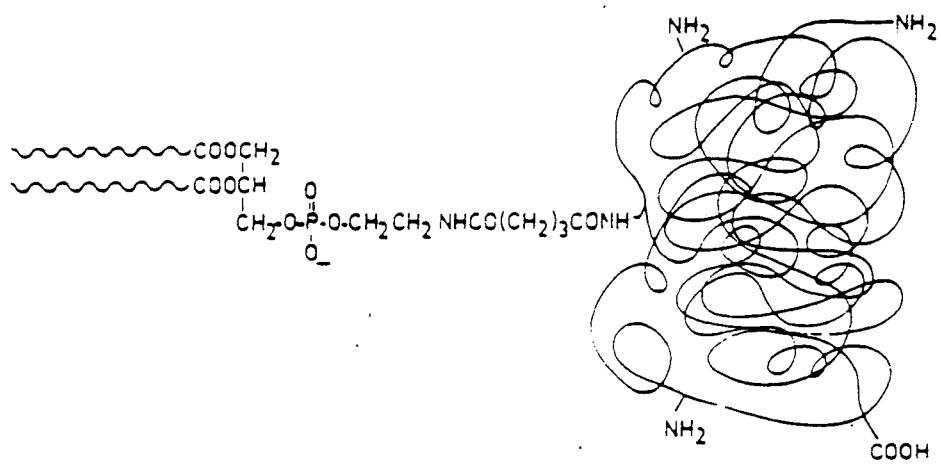
Fig. 1. Schematic representation of protein modified with N-glutaryphosphatidylethanolamine. From Weissing et al., 1986 (39).

LIPOSOME CONTAINING IMMUNOTHERAPY AGENTS FOR TREATING IGE MEDIATED ALLERGIES

This application is a continuation of application Ser. No. 092,032, filed Sept. 2, 1987, now abandoned.

BACKGROUND OF THE INVENTION

1. Field of the Invention

The present invention relates to the treatment of allergies. Allergic disorders affect as many as one in four Americans (59,000,000). More than 17% have upper respiratory allergies, including hay fever. Another 4% have asthma, and 10% have allergic skin conditions such as eczema and other rashes. It is estimated that some 40,000,000 school days are lost yearly because of asthma, in addition, approximately 6,000 lives are lost to asthma, and dozens die of insect bites, annually. The accepted allergy treatment method is hyposensitization injections containing minute amounts of allergens causing the reaction, given in incremental doses once or twice weekly until symptoms improve, and then maintained at a set dosage with decreasing frequency for approximately three years. If carefully selected, approximately one-third of patients find their symptoms are relieved substantially by this therapy. The rest have mild to moderate improvement. This immunotherapy method has been standard practice since 1911. The present invention provides a method of immunotherapy and a modified allergen extract and a method of making the modified allergen extract.

2. Description of the Prior Act

Modified allergen extracts for use in immunotherapy have been reported in the literature. Such extracts have been modified with the desire to reduce their allergenicity without sacrificing immunogenicity and hence achieve improved immunotherapy results with fewer injections. Polymerized grass pollen allergens have been prepared and tested in immunotherapy. See, Patterson et al., "Polymerization of Individual Species of Grass Pollen Allergen", *J. Allergy Clin. Immunol* 72:129-133, (1983); Fitzsimons et al., "A comparison of the Immune Response to Immunotherapy with Polymerized Grass Allergen and Monomeric Grass Allergen"; *Annals of Allergy* 57:291-294 (1986); Fitzsimons et al., supra reports that polymerized and monomeric grass pollen extract give comparable result in immunotherapy. Further reports have suggested that the polymerized grasses contain an increased amount of immunity producing allergen. It has been reported that in use a series of fifteen (15) injections with the polymerized pollen are as effective as a series of seventy (70) standard injections. Modified allergens for allergy desensitization have also been prepared by treating pollen extract with formaldehyde. Such formaldehyde treated allergens are referred to as "allergoids". Polyethylene glycol modified ragweed extracts have also been proposed for use in immunotherapy. See *Juniper, et al.* "Polyethelene Glyco - Modified Ragweed Extract: Comparison of Two Treatment Regimens". *J. Allergy Clin Immunol* 78: 851-6 (1986). See also U.S. Pat. No. 4,180,562 (Patterson) which discloses the use of ragweed polymerized extracts in immunotherapy.

Liposomes have been used in the prior art as inert carriers for drugs, enzymes, hormones and DNA. Liposomes are prepared by dispersing lipids in excess water. The lipids then assemble into spherical lipid particles called liposomes. Each phospholid molecule contains a hydrophilic (water seeking) and a hydrophobic (water avoiding) component. Therefore, when purified phospholipids are mixed with water, they spontaneously organize into bilayer structures.

Liposomes are prepared from phospholipids (e.g., sphingomyelin, lecitin and phosphatidyletanolamine) in combination with cholesterol and charged lipids such as dicetyl phosphate and stearylamine.

In the aqueous regions of a liposome, various salts, small molecules and large molecules can be trapped or encapsulated during liposome synthesis. The encapsulation of small molecules by liposomes allowed their early use as models of natural membrane functions such as complement fixation. Liposomes that are compromised by antibody and complement release the entrapped molecules, such as glucose, enzyme substrates, spin labels and chromogenic or fluorescent dyes, which can be detected by analytical methods.

Target-specific liposomes have been used as inert carriers for drugs, enzymes, hormones, DNA antigen antibodies and other biochemically important substances. Ho, R.J.Y., Rouse, B.T.; Huange, L., "Target Sensitive Liposomes Preparation and Characterization", *Biochemistry* 25: 5500-5506, 1986; Connor, J., Sullivan, S.M., & Huang, L. "Monoclonal Antibody and Liposome", *Pharmacol. Ther.* 341-365, 1985. Many techniques have been used for binding of hydrophilic proteins to liposomal surfaces. Torchilin, V.P. (1983): *Targeted Drugs* (Goldberg, E., ed.) pp. 127-152; Van Rooijen, N. and Van Nieuwmegen, R. (1981): *Targeting of Drugs* (Gregoriadis, G. ed.) Plenum, New York, NATO ASI, Series A. Among the immobilization techniques covalent modification of proteins with hydrophobic compounds which may serve as an anchor to lipid membranes seems to be the most effective. Torchilin, V.P. and Klibanov, A.L. (1981) "Preliminary 'Hyrdrophobization' of Hydrophilic Proteins Increase its Binding with Liposomes", *Enz. Microbiol. Technol.* 3, 297-304; Loelsch, R., Lasch, J., Klibanov, A.L. and Torchilin, V.P. (1981) Acta Biol. Med. Germ. 40, 331-335. In some cases the stable bilayer conformation can be obtained under physiological conditions by the addition of a second lipid component. Rand, R.P., Tinker, D.O. and Fast, P.G. (1971) *Chem. Phys. Lipids* 6, 333-342 or by the addition of certain transmembrane proteins such as glycoproteins. Ho, R.J.Y. and Huang, L. "Interaction of Antigen Sensitized Liposomes with Immobilized Antibody; a Homogenous Solid Phase Immunoliposome Assay", *J. Immunol.* 134, 4035-4040, 1985.

Liposomes have been used as vehicle to promote the immunogenicity of many antigens. Allison, A.C. & Gregoriadis, G. (1974) "Liposome as Immunological Adjuvants". *Nature* (Lond.) 252, 252. Hepatitis B surface antigen-containing liposomes enhance humoral and cell-mediated immunity to the antigen. Hedlung, G., Jansson, B. & Sjogren, H.O. "Comparison of Immune Responses Induced by Rat RT-1 Antigens Presented as Inserts into Liposomes, as Protein Micelles and as Intact Cells"; *Immunology*, 53, 69. The mechanisms by which liposomes enhance the immunogenicity of an antigen are likely to vary within different antigenic models; (i) the antigen could be present within the aqueous phase, i.e., encapsulated, and liposomes would represent a closed carrier bag ensuring a specific and efficient delivery to their natural in vivo targets, the macrophages. Alving, C.R. & Richards, R.L. (1983) "Immunologic Aspects of liposomes": *The Liposomes* (ed. M. Ostro), p. 10 Marcel Dekker, New York, Manesis, E.K., Cameron, C.H. & Gregoriadis, G. (1979) Hepatitis B Surface Antigen-Containing Liposomes Enhance Humoral and Cell-Mediated Immunity to the Antigen; *FEBS Lett.* 102, 107; Hedlung, G., Jansson, B. & Sjogren, H.O. "Comparison of Immune Responses Induced by Rat RT-1 Antigens Presented as Inserts into Liposomes, as Protein Micelles and as Intact Cells", *Immunology.* 53, 69. (ii) the liposomes could present the antigen to the immune system on a membrane-like structure the antigen is intimately associated to the lipidic lamellae. Gerlier, D., Bakouche, O., & Dore, J.F. (1983), "Liposome as a Tool to Study the Role of Membrane Presentation in the Immunogenicity of a MuLV-related Tumor Antigen", *J. Immunol.* 131, 485, or when the protein is covalently linked to the phospholipid bilayers. Snyder, S.L. & Vannier, W.E. (1984), "Immunologic Response to Protein Immobilized on the Surface of Liposomes Via Covalent Azo-bonding, *Biochem. Biophys Acta*, 772, 288; (iii) liposomes can act as a carrier in the hapten carrier system. Van Houte, A.J., Snippe, H. & Willers, J.M.N. (1979), "Characterization of Immunogenci Properties of Haptenated Liposomal Model Membranes in Mice", *Immunology*, 37, 505.

The presence of some cholesterol within the phospholipid bilayers increased the immunogenic properties of GCSAa liposomes as well as that of haptened liposomes. Van Houte, A.J., Snippe, H., Schmitz, M.G.J., & Willers, J.M.N. (1981), "Characterization of Immunogenic Properties of Haptenated Liposomal Model Membranes in Mice, V. Effect of Membrane composition on Humoral and Cellular Immunogenicity", *Immunology*, 44, 561. The addition of a negatively charged phospholipid as a minor component was followed by an increase in the immunogenicity of the antigen-liposome complex. Heath, T.D., Edwards, D.C. & Tyman, B.E. (1976), "The Adjuvant Properties of Liposomes", *Biochem. Soc. Trans.* 4, 129.

SUMMARY OF THE INVENTION

The presence of IgE in patient serum was recognized as an indication of allergic disease in 1967 by Johannson and Bennich. Control of IgE mediated disease is believed to require a suppression of IgE production in the body. According to the present invention, modified allergy immunotherapy agents are supplied which in use result in a suppression of the production of IgE in response to the allergen and a stimulation of the production of IgG against the allergen.

The present invention provides highly effective immunotherapy agents for treatment of IgE mediated allergies, a method of making the allergy immunotherapy agents and a highly effective immunotherapy regimen. Examples of substances that are known allergens abound. For example, milk, house dust, ragweed, grass pollen, tree pollen, fish, dog dander, cat dander, horse dander, bee venom, wasp venom, chocolate and eggs are common allergens.

According to the invention, a combination of allergen and liposome is provided. The liposomes according to the invention, are prepared from any appropriate lipid or phospholipid source. Examples of phospholipid sources include lecitin, sphingomyelin; and phosphatidyletanolamine preferably in combination with cholesterol. Lipid source includes dicetylphosphate and stearylamine. The liposome is optionally but preferably linked to the allergen by covalent bonds. Preferably a biological response modifier (BRM), as described in my co-pending application Ser. No. 65310 filed June 23, 1987 which is incorporated herein by reference is also combined with the liposome allergen combination. such biological response modifier is selected from the group of cytokines, bacterial immunopotentiators, viral immunopotentiators, fungal immunopotentiators and thymic factors. The allergen and BRM can be combiend with the liposome separately or as allergen-BRM conjugate or mixture can be combined with the liposome. Thus, the allergen and the BRM are encapsulated in, mixed with or covalently bound to a liposome. The use of the immunotherapy agents of the invention will result in more effective immunotherapy and allow a substantial reduction in the number of injections to achieve a comparable degree of immunotherapy compared to immunotherapy performed with conventional allergen extracts.

The preferred embodiment of the present invention is illustrated in the drawings and Examples. However, it should be expressly understood that the present invention should not be limited solely to the illustrative embodiment.

FIG. 1 is a schematic presentation of protein modification with N-glutarylphosphalidylethanolamine (N-GIU-PE).

DETAILED DESCRIPTION OF THE INVENTION

In accordance with the present invention it has been found that a highly effective immunotherapy agent is provided by the combination of an allergen to which a patient is allergic and a liposome. This improvement is heightened when the liposome is combined with a biological response modifier as well as with the allergen. Improved immunotherapy results can be obtained by using the combination of allergen and liposome and the combination of allergen, liposome and BRM. According to the invention, the allergen is preferably either crosslinked to the liposome or is encapsulated by the liposome. The bioligical response modifiers (BRM's), used in accordance with the claimed invention are preferably selected from the group of cytokines, bacterial immunopotentiators, viral immunopotentiators, fungal immunopotentiators and thymic factors. Useful in the subject invention is a combination of allergen BRM as shown in my co-pending application, Ser. No. 065,310 filed June 22, 1987.

The liposome allergen product is preferably either an allergen covalently bound to the liposome or an allergen encapsulated within the liposome.

Conjugation of Allergens and/or BRM's to Liposomes

A variety of conjugation procedures have been applied to the conjugation of liposomes to antigens. See Connor, *Supra Pharmacol. Ther.* 28, 341-65 (1985). These procedures are generally applicable to conjugation of the products according to the invention.

According to the invention, the liposomes can be conjugated to the allergen or BRM in a variety of ways. For example, a first technique is a covalent chemical crosslinking between a liposomal lipid and a native or modified allergen or BRM; this is achieved by use of a homo or heterobifunctional crosslinking reagent which reacts with specific functional groups on the phospholipid and the allergen. A second technique involves a covalent derivatization of the allergen with a hydrophobic anchor, such as fatty acids, followed by incorporation into preformed liposomes. The wide applicability of these two techniques make it possible to associate most allergens with a variety of different liposomes.

Cross Linking Techniques

When preparing immunoliposomes by the crosslinking technique, a variety of available reagents can be employed to produce the covalent link between the lipid and the allergen. One basic technique is to derivatize the free amino group of a phosphatidylethanolamine (PE) with an amino reactive bifunctional crosslinker. The derivatized PE along with other appropriate lipids are then used to form liposomes by the methods previously described. The mol % of derivatized PE used is a controlling factor in the amount of allergen or BRM's which can be attached to each liposome. Once incorporated into the liposome the derivatized PE can be reacted with the antigen by use of the second reactive site on the crosslinking reagent. In this scheme heterobifunctional reagents are particularly useful because homocoupling between liposomes or between allergen or BRM's can be avoided.

A crosslinker N-hydroxysucciimidyl 3-(2-pyridythio) propionate (SPDP) which reacts with amino groups on both PE and the respective allergen and/or BRM is used. The allergen and/or BRM component is then reduced with dithiothreitol at pH4.5, yielding a free thiol group. This free thiol will crosslink with the derivatized PE via a disulfide exchange reaction. A similar protocol has been employed with both IgG and Protein A, Barbet, (1982), Methodologie de Liposomes, pp. 141–150. INSERM, Paris, shown as Reaction 1 below.

activated PE will crosslink to free sulfhydryl groups on the reduced allergen or BRM. A similar technique has been previously employed to attach rabbit FAb and a mouse monoclonal IgM to liposomes as shown in Reaction 2. Martin, (1982), J. biol. Chem 257: 286–288.

REACTION 2

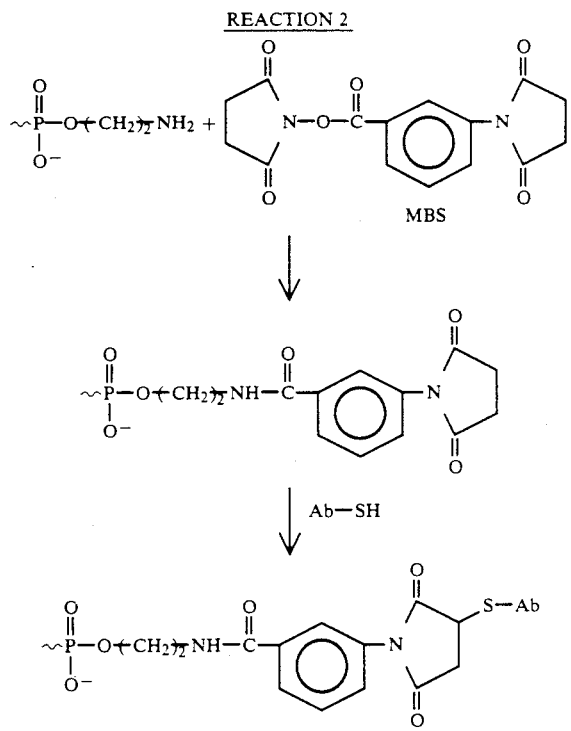

REACTION 1

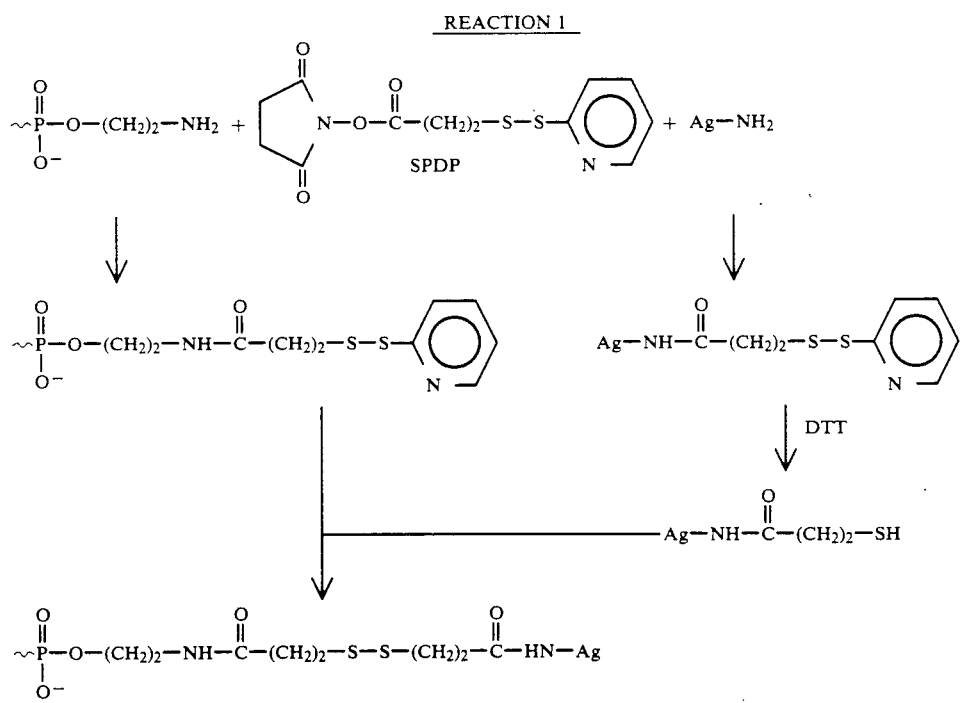

Another heterobifunctional crosslinker is m-maleimidobenzoyl-N-hydroxysuccinimide ester (MBS). This reagent reacts with the amino group of PE and a sulfhydryl functional group on a reduced allergen. In this technique, PE is first derivatized with MBS to yield a phospholipid with a reactive maleimide head group. The modified PE is incorporated in vesicles and the Alternatively, allergens and BRM's can be directly crosslinked to liposomes in a one step reaction by using homobifunctional crosslinking reagents. In this technique preformed liposomes, containing PE, are mixed with the appropriate allergen or BRM in the presence of the crosslinker, which will covalently attach the allergen or BRM to the vesicle in a single step reaction. Toluene-2, 4-diisocyanate (TDIC) can simultaneously react with the amino groups of PE and the allergen. This reagent has been used to crosslink dansyl-BSA to liposomes, Endoh, (1980), J. Immun. Meth. 36: 185-192.

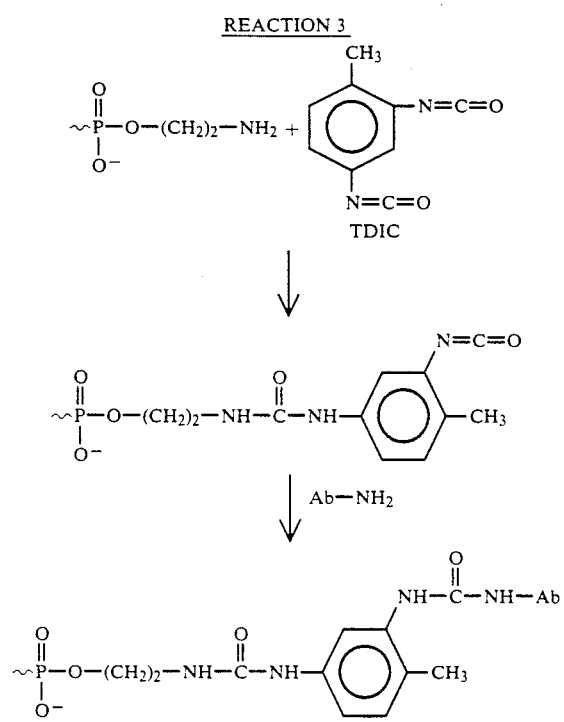

Another direct crosslinker which can be used to link allergen or BRM to liposome is 1-ethyl-3-(3-dimethylaminopropyl) carbodiimide (EDCI). This request has been previously used to link IgG to liposome as shown in Reaction 4, Endoh, (1981), J. Immuno. Meth. 44: 79-85.

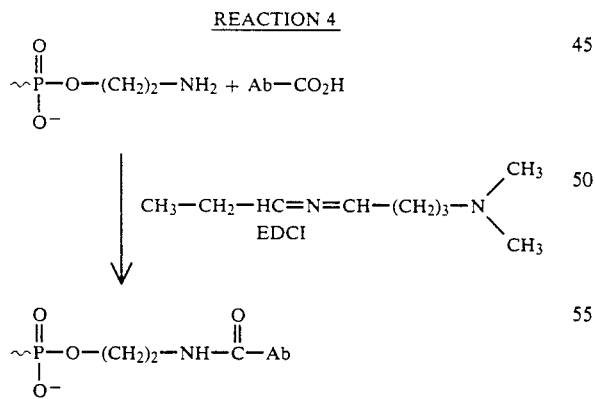

The second technique involves a different approach than the chemical crosslinking technique. According to the second technique a free aldehyde functional group on the phospholipid component is produced. This can be achieved by periodate oxidation of phosphatidylinositol (PI) phosphatidylglycerol (PG) or ganglioside, whose carbohydrate component is converted to free aldehyde groups, as shown in Reaction 5 described in Heath, (1980a), Fedn. Proc. 39: 1985-1991.

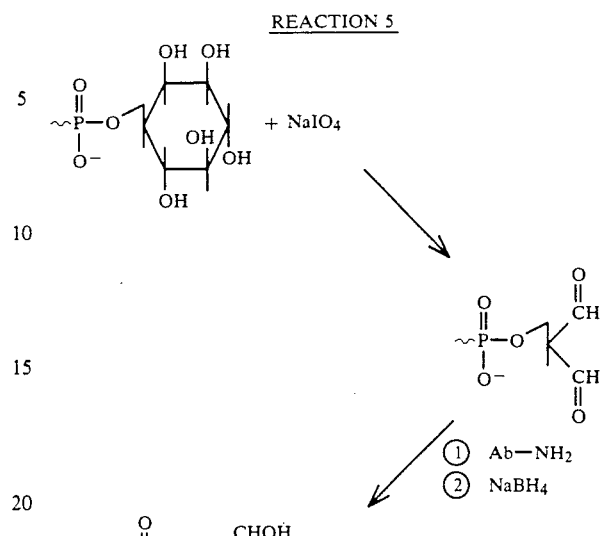

Another scheme is to derivatize a liposomal PE molecule with glutaraldehyde which will bind with the PE amino group leaving a free aldehyde group on the distal side of the glutaraldehyde, Torchilin, V.P., (1978), Biochem biophys. Res. Commun. 85: 983-990. Reaction 6 from Torchili, (1978), Biochem biophys. Res. Commun. 85: 983-990. The free aldehyde on the modified lipid is capable of forming a Schiff's base with the &-amino groups of the antigen. Sodium borohydride or sodium cyanoborohydrite treatment reduces the Schiff's base to a stable secondary amino bond creating a covalent crosslinkage between the antibody and the liposome. The use of glutaraldehyde allows for a three carbon linker between the lipid head group and the protein. This provides better flexibility when the proceeding is used to bind an allergen

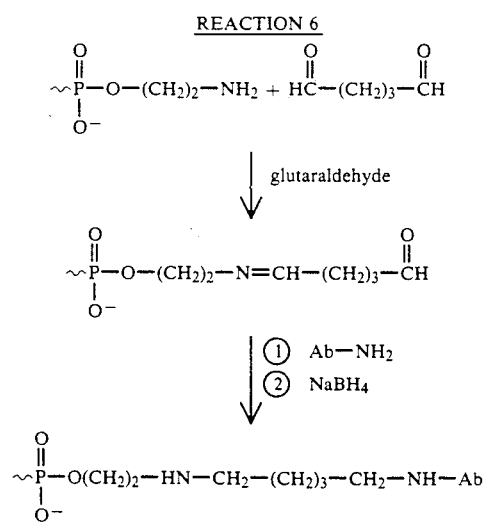

Allergen Derivatization and Incorporation Into Liposomes

The technique of a non-crosslinking association of allergen with liposomes involves the derivatization of the allergen component with a hydrophobic group. The derivatized allergen can then be incorporated into vesicles by the insertion of the hydrophobic anchor into the bilayer. One commonly used hydrophobic group is the free fatty acid, such as palmitic acid.

The derivatization of allergen is achieved by reacting the protein with the N-hydroxysuccinimide ester of palmitic acid (NHSP) in the presence of 1-2% detergent, typically deoxycholate (DOC). Alternatively palmitic acid chloranhydride can replace NHSP as the acylation reagent. This reaction attaches the hydrophobic palmitoyl chain to an amine on the protein via a stable amide bond. See (Reaction 7 from Huang, Biochem. biophys. Acta 716: 140-150).

REACTION 7

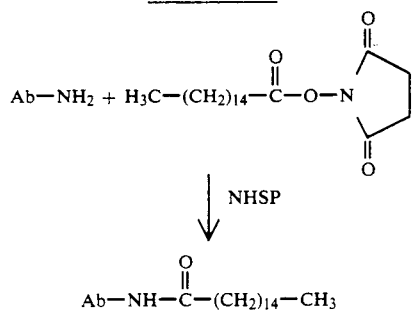

A second method to acylate a protein involves derivatizing the head group of a PE molecule rendering it capable of reacting with a sulfhydryl group. Through a series of reactions PE is derivatized to N-(N-a-icdoacetyl, N-e-dansyl-lysyl) PE (iodo DLPEA). This technique was reported using Bence-Jones proteins. The protein disulfide bonds are first reduced with DTT, followed by an incubation with the iodo DLPEA in alkaline conditions (Reaction 8 from Sinha. Biochem. biophys. Res. Commun 90: 554-560). This yielded monomeric DLPEA conjugated to the Bence-Jones proteins.

REACTION 8

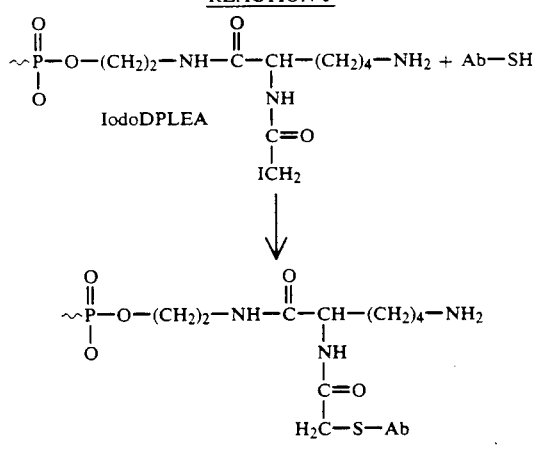

An additional method for attaching PE as a hydrophobic anchor is to crosslink a free PE molecule to the carboxylic groups of allergen or BRM by carbodiimide. The free amino groups of the allergen or BRM have to be protected by citraconic anhydride prior to the CDI crosslinking of PE to the carbohydrate in order to prevent homocoupling between antigens. (See Reaction 9 from Jansons, (1981), Analyt. Biochem. 11: 54-59).

The use of NHSP to derivative IgG has been well characterized in order to optimize the coupling conditions. Using anti-H2K$^k$, an antibody to the murine major histocompatability antigen, a ratio between NHSP and IgG of 10 to 20 was determined to be optimal; this ratio yields 3-4 palmitoyl chains per IgG molecule. These conditions caused only about a 3-4-fold decrease in antigen binding capacity. By controlling the stoichiometry of the reactants and the coupling conditions the extent of derivatization and therefore the antigen binding ability can be precisely controlled.

REACTION 9

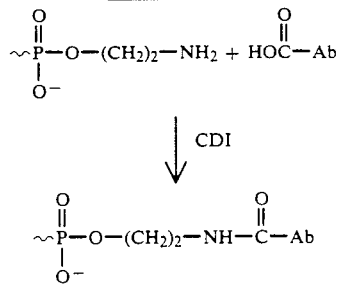

EXAMPLES

Preparation of Allergens Associated with Liposomes (Allergosomes)

Allergosome is an expression coined by applicants for covalent binding, attachment or encapsulation of allergens with different liposomes. This encapsulation of liposomes can be with proteins or haptens of allergens alone, or in combination with a variety of biological response modifiers.

EXAMPLE 1

Material and Methods

D-L-x-dilauroylphosphatidylcholine (DLPC, C12:0-R-C12:0),

D-L-x-dimyristoylphosphatidylcholine (DMPC, C14:0-R-C14:0),

D-L-x-dipalmitoylphosphatidylcholine (DPPC, C16:0-R-C16:0),

L-x-diheptadecanoylphosphatidylcholine (DHPC, C17:0-R-C17:0),

D-L-x-distearoylphosphatidylcholine (DSPC, C18:0-R-C18:0:,

D-L-x-dioleylphosphatidylcholine (DOPC, C18:1-R-C18:1),

L-x-dilinoleoylphosphatidylcholine (DLiPC, C18:2-R-C18:2),

L-x-B-palmitoyl-y-lineolecylphosphatidylcholine (PLiPC, C16:0-R-l6:0-R-C18:2),

L-x-dipalmitoylphosphatidylglcerol (DPPG, C16:0-R-C16:0),

L-x-dipalmitoylphosphatidylethanolamine (DPPE, C16:0-R-C16:0),

L-x-dimyristoylphosphatidylethanolamine (DMPE, C14:0-R-C14:0), dicetylphosphate (DCP and cholesterol were purchased from Sigma Chemical Co., St. Louis, MO.)

Allergens

Standardized allergens were purchased from PHARMACIA, some of which were labeled with iodine by NMS Pharmaceuticals. IL1 and IL2 were purchased from Genzyme Inc. and were labeled by NMS Pharmaceuticals with iodine. Corynebacterium Parvum antigens were purchased from RIBI Immunochemicals, Candida antigen was prepared in our laboratory and was labeled with iodine by NMS Pharmaceuticals.

Preparation of Liposomes

Conventional multilayered vesicles (MLV) were prepared by hydrating with excess PBS lipid films that had been predried onto the bottom of 100 mL round-bottom flakes. Stable plurilamellar vesicle (SPLV) vesicles were prepared as described by Pidgeon et al., 1987, *Biochemistry* 26:17. For solid lipid mixtures (dipalmitoylphosphatidy-choline (DPPC) cholesterol (CH) 9:1), SPLVS were also prepared from diisopropyl ether and the vesicle were heated to 50° C. during or after liposome formation. SPLV and MLV liposomes were washed and purified by centriguation as described under MLV-REV (MLV prepared by the reverse-phase evaporation method) preparation MLV-REV Preparation: Fluid Lipids. Fluid lipids used to prepare MLV-REV liposomes utilized egg phosphatidylcholine (PC) as the predominant membrane-forming lipid; cholesterol, dipamitoylphosphatidylcholine MLV-REV vesicles were prepared according to *Pidgeon* et al., 1986, *Pharm. Res.* 3, 23-24. Thus, ether solutions (10 mL) of lipid were emulsified with PBS solutions (0.3 or 0.5 mL) of drug by 1-2 min of sonication under nitrogen. Emulsion ether was removed at 30° C. in two stages. Stage 1 required 9+3 min at 400 mmHg to form a gel. The vacuum was broken, and the gel was vortexed for about 5 s. Gel inversion to liposome formation, stage 2, required lowering the vacuum at 50-mmHg increments (2 min/interval) from 400 to 100 mmHg; approximately 16+2 min was needed to form the vesicles. When required 50-300 uL of sterile water was added to the gel before stage 2 was initiated.

The flask was rapidly rotated during the rotoevaporation of the emulsion at stages 1 and 2. After stage 2, the viscous liposome suspension was diluted to 1.5 mL with PBS and transferred to microfuge tubes. Liposomes were separated from unentrapped aqueous space markers by 10-15 min of centrifugation in a microfuge (12000 rpm). Liposomes containing CH, PS, PA and PG required 20-25 min of centrifugation.

After centrifugation, vesicles were suspended in excess of PBS and centrifuged again. This vesicle purification process was performed at least 3 times for all vesicles. For some experiments vesicles were pelleted at 12000 rpm in a Sorvall LL-3 automatic centrifuge instead of a microfuge.

Radiolabeled protein markers were used to quantitate the amount of protein entrapped. The amount of allergen entrapped was always corrected for lipid recovery, and therefore, protein entrapment values reflect the theoretical values if 100% of the lipid was recovered throughout the purification process. Typically, lipid losses were less than 10%.

EXAMPLE 2

Preparation of Allergosomes by Crosslinking Technique

A. Preparation of liposomes conjugated with allergens.

Amino group-bearing liposomes were prepared as follows. A lipid film consisting of sphingomyelin (SM) (10 umole), cholesterol (Chol)(5umols), phosphatidylethanolamine (PE) (2) umole), dicethyl phosphate (DCP) (2 umole), and ]$^3$H] triolein (2.5 uCi) was dispersed with 10 ml of PBS containing 10% of Ficoll (Pharmacia Fine Chemicals, Uppsala, Sweden). To 2 ml of the liposome suspension was added 20 ul of a 2% solution in p-dioxane of tolylene-2,4-diisocyanteae (TDIC, Tokyo Chemical Industry, Tokyo, Japan). The reaction mixture was incubated at 17° C. for 2 h with shaking. Polymerized material derived from TDIC was removed from this mixture by centrifugation at 400×g for 5 min. The resulting supernatant was then mixed with 1 ml of June Grass solution (20 mg/ml in PBS) and incubated at 37° C. for 2 h to produce June Grass-modified liposomes. To separate noncovalently bound protein, 8 ml of PBS containing 0.02% of EDTA was added to the mixture and the liposomes were collected by centrifugation at 750×g for 20 min. The liposomes were further washed 5 times with 10 ml of PBS using the same centrifugation. The final recovery of liposomes was in the range 65-85%. Controls for this reaction were prepared in the absence of TDIC and/or using PE-free liposomes. Similarly, other proteins with immune augmentation capability were bound to these liposomes.

B. Binding of Glycoproteins to Liposomes

For binding of carbohydrates to liposomes different approach to the chemical crosslinking was used. First periodate oxidation of glycoproteins from Candida Albican, Corynebacterium Parvum or methanol extract of Bacillus Calmette Guerin (BCG) was achieved and the carbohydrate components were converted to free aldehyde group as generally described in *Torchilin* 1982, *FEBS LETTER* 138:117-120. This aldehyde group binds with the amino group of phospholipid which by addition of sodium borohydride treatment reduces to a stable secondary amino bond creating a covalent crosslinkage between the immunemodulator and the liposome according to Reaction 10.

REACTION 10

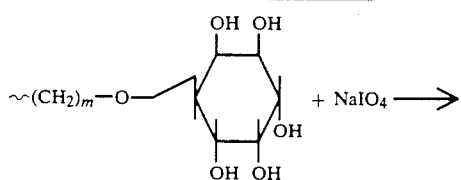

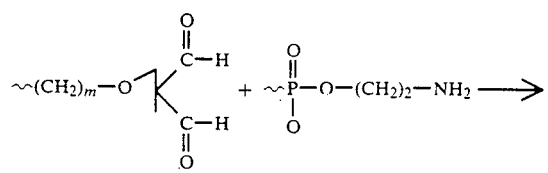

-continued
REACTION 10

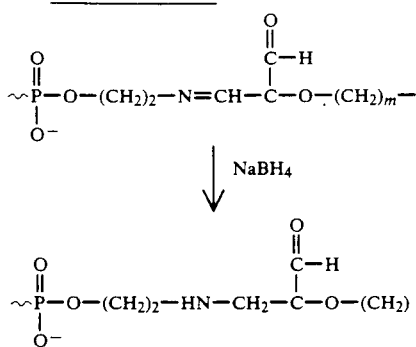

EXAMPLE 3
Preparation of Allergosomes by Non-Crosslinking Association of Allergens with Liposomes The hydrophobic anchor method of Weissin et al., 1986 FEBS LETTER 202:86 was modified for the attachment of allergens to lipsomal membranes. Briefly, 20 mg of N-glutarylphosphatidylethanolamine was suspended in 150 ml DMSO, followed by addition of 2 ml of 0.15 M Na-Cl solution. After 15 seconds sonication, the pH was adjusted to 3.5 and 30 mg 1-ethyl-3-(3-dimethylaminopropyl) carbodiimide was added after 5 min, 1 ml of solution of either June Grass or C. Parvum glycoprotein (40 mg/ml in 0.1M borate buffer, pH 8.5) was added and the mixture incubated for 2 hours at 4° C. Pure egg phosphatidylcholine final concentration 15 mg/ml were prepared by reversed-phase evaporation.

The desired mixture of different phospholipids is dissolved in an organic solvent and is then deposited as a thin film on the inside surface of a round bottom flask by reverse phase evaporation of the solvent. Also, multilayered vesicle preparation by reverse-phase evaporation for optimal protein entrapment was used, Pidgeon et al., 1987 (Supra).

The lipid was emulsified in 3 ml of diethylether and 1 ml of aqueous solution of modified proteins was added. In addition, 20 ml of a solution of calcein (40 mm in 0.1 m Nacl. 10 mm Hepes) were included to check the integrity of the liposomes. Unbound antigens were separated from the liposomes by flotation in a discontinous sucrose and ficoll gradient centrifugation. Iodine labeled protein and glycoprotein markers were used to quantitate the amount of allergen entrapped. The amount of allergen entrapped was between 63–78%.

FIG. 1 is schematic presentation of protein modification with N-glutarylphosphatidylethanolamine (N-GLU-PE). N-GLU-PE reacts in the presence of water soluble carbodiimided with free amino group of proteins to form amide bonds.

Using a combination of these techniques, the following liposomes were prepared.

1. Phosphatidylcholine Associated June Grass
2. Phosphatidylcholine Associated C. Parvum Antigens
3. Phosphatidylcholine Associated June Grass+C. Parvum Antigens.
4. Phosphatidylcholine covalently bound to chemically modified June Grass.
5. Phosphatidylcholine covalently bound to modified C. Parvum antigens.
6. Phosphatidylcholine covalently bound to modified June Grass +C. Parvum antigens.

EXAMPLE 4
Effects of June Grass associated liposomes on histamine basophil release and IgE, IgG synthesis in-vitro.

Measurement of basophil histamine release and synthesis of allergen specific IgE and IgG was performed. Human mononuclear cells from allergic and normal donors were separated, using ficoll density gradient centrifugation. After separation and counting $2 \times 10^6$ cells were initially incubated in 2 mil glutamine, streptomycin, 0.25 ug fungizone/ml) or complete medium (consisting of RPMI 1640 supplemented with 2 m M glutamine, streptomycin, 0.25 ug fungizone/ml) or complete medium (consisting of basic medium without tryptic soy broth but supplemented with 15% heat inactivated pooled human AB serum) with or without 10, 100 and 1000 ug/ml of June Grass or the same amount of June Grass associated liposomes and liposomes associated with similar concentrations of June Grass plus 100/ug of corynebacterium parvum antigens) as a biological response modifiers.

At day 1, 4 and 10 samples were removed and centrifuged at 500 g. Using staining techniques, numbers of lymphocytes and basophils were counted in the pellet and the supernatant was removed for measurements of histamine content and allergen specific IgE and IgG.

Measurement of Histamine

Histamine was measured, using a competitive RIA technique as follows

Histamine RIA: The histamine content of the supernatants is determined by a competitive binding radioimmunoassay with second antibody separation of antibody-ligand complexes. The assay is linear between 2 and 100 ng/ml histamine. 50 ul of supernatant is incubated at room temperature for 30 minutes with 100 ul of 3 H-histamine tracer and 100 ul anti-histamine antibody. 200 ul of precipitating second antibody is added. After 30 minutes at refrigeration temperature the duplicates tubes are centrifuged in a refrigerated centrifuge. The supernatant is aspirated and the pellet dissolved with NaOH. Scintillation cocktail is added and the radioactivity is determined in a liquid scintillation counter. Haydik I.G. "Histamine Determination by Radioimmunoassay", J. Allergy Clinical Immunology 71:152, 1983.

Measurement of Allergen Specific IgE and IgG 100 ul of supernatant was transferred into U-bottom microtier plates, precoated with the allergen (June Grass), and incubated for 1 hour at room temperature. Supernatants were then decanted and wells washed 3 times with 1% BSA in Dullbecco's phosphate labelled anti human IgE or IgG were added to each well. After another hour of incubation at room temperature, anti IgE or anti IgG were decanted and the wells washed 3 times with 0.5% BSA in PBS. After 60 minutes, from addition of substrate P-nitrophenyl phosphate color development measured at 405 mM and the amount of allergen specific IgE or IgG was expressed by titer. Titer is the last dilution of serum giving twice absorbence of the control well.

Results from 20 different allergic patients clearly showed that soluble June Grass induced basophil histamine release (day 1) and production of a significant amount of IgE (day 4) in vitro. Simultaneously low levels of IgG anti June Grass were detected at day 10 of the cultures. But when the allergen(s) were associated or covalently bound to liposomes and were added to the leukocyte cultures, neither histamine release occurred nor allergen specific IgE was produced. Contrary to the soluble allergen, allergosomes induced a significant amount of IgG. From these results one can conclude that June Grass binding to liposome(s) with or without biological response modifiers resulted in significant modification and regulation of cellular events which lead to production of IgG but not IgE (Table 1).

TABLE I

| Allergens | Basophil Histamine Release | IgE Production In Vitro | IgG Production In Vitro |
|---|---|---|---|
| Soluble June Grass 100/ug/ml | +++ | +++ | + |
| Liposomes Control | — | — | — |
| Corynebacterium Parvum | ± | — | — |
| June Grass Associated Liposomes | — | ± | +++ |
| June Grass Cross Linked Liposomes | — | — | +++ |
| June Grass and Corynebacterium Parvum Antigens Associated Liposomes | — | — | +++ |

Note to Table I.
Binding of June Grass to liposomes which increase its antigenicity but decrease its allegenicity.
Different patients' lymphocytes with class 5 RAST to June Grass were mixed with different concentrations of June Grass or June Grass bound to liposomes. The mixture was incubated at 37° C. with 5% $CO_2$ and 95% air for a period of 10 days. At different intervals (1, 4, 10 days) samples from culture medium were removed and examined for histamine. IgE and IgG specific antibodies. The highest amount of histamine was detected at day one and IgE and IgG at day 4, 10 respectively.

EXAMPLE 5

Effects of June Grass and June Grass Associated Liposomes on IgG Production in vivo:

A group of rabbits were immunized each separatedly with subcutaneous injection of 2 mg (protein) of soluble June Grass, June Grass crosslinked to liposomes or June Grass and Corynebacterium Parvum crosslinked liposome.

At days 1, 7, 14, 21, 28, 35 and 42 post single injection, blood was collected and antibody titer was determined using precoated plates with optimal concentration of June Grass. Results summarized in Table II clearly showed that rabbits injected with 2 mg of soluble June Grass antigens, produced low levels of IgG antibodies, while the same antigens crosslinked to liposomes provoked 4 folds of antibody production. Moreover, if in addition to June Grass, biological response modifier such as corynebacterium parvum antigen(s) was crosslinked to the same liposomes, antibody production was increased more than 15 folds (Table II).

TABLE II

Effects of June Grass and June Grass liposomes on IgG production in vivo.

| | IgG Antibody Titers Against Different Antigens | | |
|---|---|---|---|
| Days Post Antigen Injection | Soluble June Grass | June Grass Cross Linked to Liposome | June Grass and C-Parvum Cross Linked Liposomes |
| 1 | 4 | 4 | 4 |
| 7 | 8 | 4 | 8 |
| 14 | 8 | 64 | 8 |
| 21 | 8 | 64 | 64 |
| 28 | 16 | 128 | 256 |
| 35 | 64 | 512 | 1024 |
| 42 | 32 | 256 | 2056 |

Different rabbits were injected with 2 mg of soluble June Grass antigens or 2 mg of June Grass angigens bound to liposomes with or without biological response modifier. Different days post injection serum was prepared and was measured by Elisa for the specific levels of IgG against soluble June Grass.

It should be understood by those skilled in the art that various modifications may be made in the present invention without departing from the spirit and scope thereof, as described in the specification and defined in the appended claims.

I claim:

1. An allergy immunotherapy agent comprising liposome, an allergen which causes an IgE mediated allergy and a BRM derived from Corynebacterium Parvum.

2. An immunotherapy agent according to claim 1 wherein the allergen is covalently linked to the liposome.

3. An immunotherapy agent according to claim 1 wherein the BRM is covalently bound to said liposome.

4. An immunotherapy agent according to claim 1 wherein the liposome is derived from licithin, sphingomyelin, phosphatidyletanolamine, dicetylphosphate, stearylamine or cholesterol.

5. An immunotherapy agent according to claim 4 wherein the liposome is phosphatidylcholine.

6. A method of allergy immunotherapy comprising periodically injecting an allergic person with an immunotherapy agent composed of an allergen which causes an IgE mediated allergy i the allergic person said allergen encapsulated in or covalently linked to a liposome and a BRM derived from Corynebacterium Parvum encapsulated in or covalently linked to said liposome.

7. A method according to claim 6 wherein said BRM is covalently bound to the liposome.

8. A method according to claim 6 further comprising mixing a pharmaceutically acceptable carrier with said immunotherapy agent before injecting.

9. A method according to claim 6 wherein said allergen is covalently bound to said liposomes.

10. A method according to claim 6 wherein both said BRM and said allergen are covalently bound to said liposome.

11. A method of enhancing production of allergen specific IgG in a mammal comprising injecting the mammal with a therapeutically effective amount of an allergen, and a BRM derived from Corynebacterium Parvum encapsulated in or covalently bound to a liposome.

* * * * *